United States Patent [19]

Funke et al.

[11] Patent Number: 4,920,965

[45] Date of Patent: May 1, 1990

[54] DUAL CHAMBER PACEMAKER WITH ADAPTIVE ATRIAL ESCAPE INTERVAL

[75] Inventors: Hermann D. Funke, Bonn, Fed. Rep. of Germany; Jozef H. Lodew k, Kerkrade, Netherlands

[73] Assignee: Medtronic, Inc., Minneapolis, Minn.

[21] Appl. No.: 125,424

[22] Filed: Nov. 25, 1987

[51] Int. Cl.⁵ .............................................. A61N 1/36
[52] U.S. Cl. ............................................... 128/419 PG
[58] Field of Search .................................. 128/419 PG

[56] References Cited

U.S. PATENT DOCUMENTS

| | | | |
|---|---|---|---|
| 3,747,604 | 7/1973 | Berkovits | 128/419 P |
| 4,091,817 | 5/1978 | Thaler | 128/419 PG |
| 4,429,697 | 2/1984 | Nappholz et al. | 128/419 PG |
| 4,503,857 | 3/1985 | Boute et al. | 128/419 PG |
| 4,515,161 | 5/1985 | Wittkampf et al. | 128/419 PG |
| 4,539,991 | 9/1985 | Boute et al. | 128/419 PG |
| 4,554,921 | 11/1985 | Boute et al. | 128/419 PG |
| 4,562,841 | 1/1986 | Brockway et al. | 128/419 PG |
| 4,624,260 | 11/1986 | Baker, Jr. et al. | 128/419 PG |
| 4,714,079 | 12/1987 | Hedberg et al. | 128/419 PG |

FOREIGN PATENT DOCUMENTS

WO86/05698  10/1986  PCT Int'l Appl. .......... 128/419 PG

*Primary Examiner*—Lee S. Cohen
*Assistant Examiner*—Scott Getzow
*Attorney, Agent, or Firm*—Reed A. Duthler; Robert J. Klepinski; Joseph F. Breimayer

[57] ABSTRACT

A dual chamber pacemaker having an atrial escape interval which is varied on a beat-to-beat basis in response to the measured time from a ventricular event to the next atrial sensed event. Additionally, a portion of the atrial escape interval is bifurcated into a first sensing portion T1 and a second sensing portion T2 wherein atrial sense events occurring during T1 may be ignored by the pacemaker, while atrial sense events falling within T2 are used to compute a new atrial escape interval and are used to resynchronize the pacemaker and are used to inhibit the otherwise scheduled atrial pace event.

21 Claims, 6 Drawing Sheets

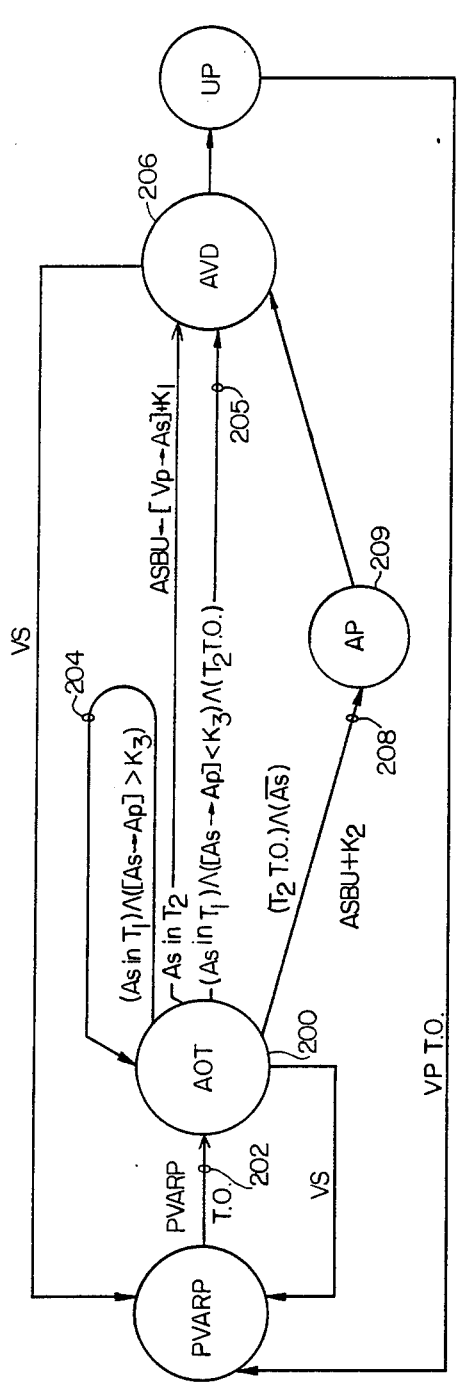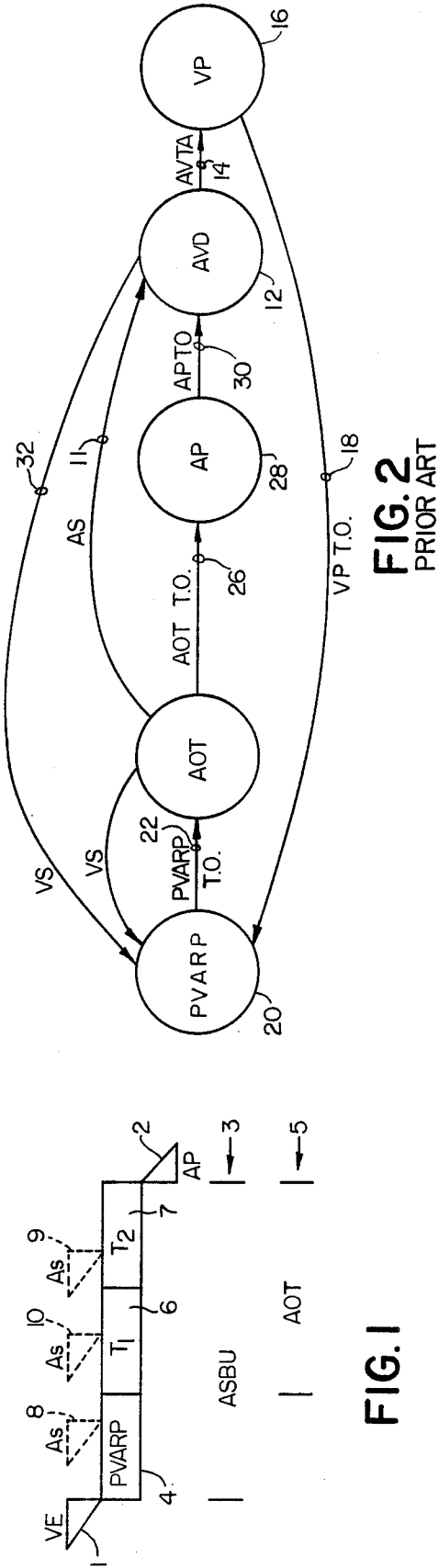

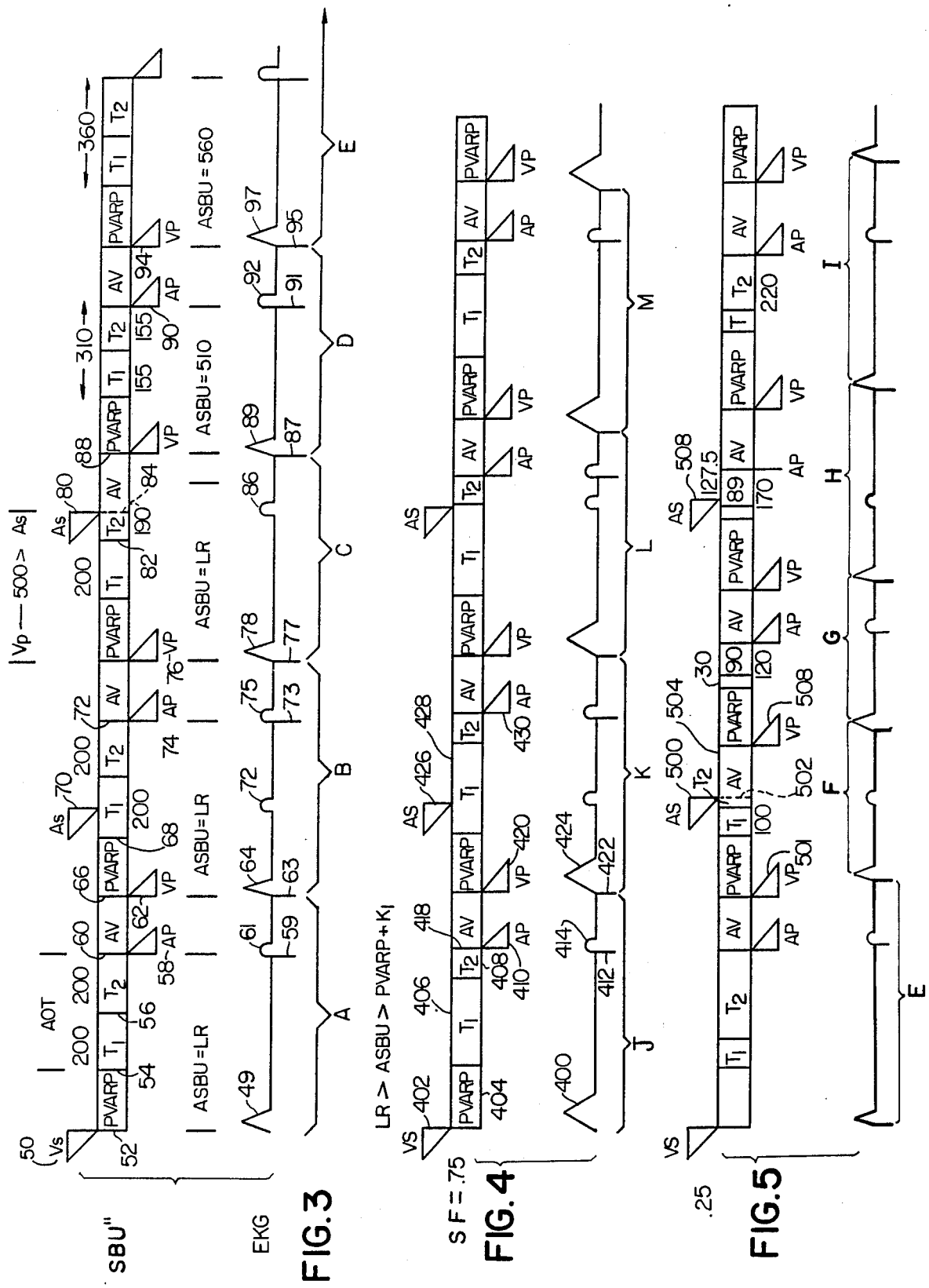

DUAL CHAMBER PACEMAKER WITH ADAPTIVE ATRIAL ESCAPE INTERVAL

BACKGROUND OF THE INVENTION

1. Field of the Invention

The invention relates to cardiac pacemakers and more particularly to a dual chamber pacemaker which varies the pacer V-A escape interval in response to the timing of the patient's atrial activity.

2. Description of the Prior Art

The first pacemakers were asynchronous. these VOO mode pacemakers are typified by U.S. Pat. No. 3,057,456 to Greatbatch. Such pacers operate independently of intrinsic heart activity and pace the ventricle at a metronomic rate. Although such pacemakers provide a ventricular pacing rate sufficient to support life, these pacemakers can compete with intrinsic ventricular rhythms which can prove hazardous to the patient.

The VVI mode or ventricular demand pacemaker, as typified by U.S. Pat. No. 3,478,746 to Greatbatch, was introduced to reduce competitive pacing with naturally occurring ventricular rhythms. This ventricular inhibited form of pacemaker provides a ventricular sense amplifier responsive to ventricular depolarizations. The ventricular sense event recycles the V-V timer of the pacemaker. At the conclusion of the V-V time interval, the pacemaker stimulates the ventricle unless inhibited from doing so by a ventricular sense event occuring within the V-V interval.

The VAT mode pacemaker as typified by U.S. Pat. No. 3,254,596 to Keller provides an atrial sense amplifier responsive to atrial depolarizations which starts an A-V timer within the pacemaker. At the conclusion of this A-V time interval, the pacemaker generates a ventricular pacing pulse which is delivered to the ventricle. This stimulus is synchronized with the naturally occurring atrial beat. Therefore, this atrial synchronized form of ventricular pacemaker provides a prosthetic conduction pathway mimicking the natural pathway of the heart by providing a paced ventricular rhythm in response to and synchronized with the detected atrial rate. A defect of this pacing modality is the ability to compete with ectopic ventricular activity. An ectopic ventricular beat will be sensed in the atrium and treated as though it were an atrial event. This will result in the generation of a ventricular pacing stimulus a fixed A-V delay after the atrially detected ventricular event. Although such competitive pacing is considered harmless when the A-V delay of the VAT pacemaker is short, such a pacing regime can result in delivery of a ventricular pacing stimulus into the vulnerable period of the R-waves which is undesirable.

The VDD mode pacemaker, as typified by U.S. Pat. No. 3,648,707 to Greatbatch, overcomes this drawback of the VAT mode pacemaker by providing a ventricular sense amplifier responsive to ventricular depolarizations for inhibiting an otherwise scheduled ventricular pacing event by the pacemaker. In operation, the VDD pacemaker may sense atrial depolarizations through an atrial sense amplifier which starts an A-V timer. The A-V timer schedules the generation of a ventricular pacing pulse one A-V interval after the detected atrial signal. The scheduled stimulation, however, may be interrupted or inhibited by the detection of a naturally occurring ventricular event detected by the ventricular sense amplifier. In the absence of either atrial or ventricular rhythms, the VDD pacemaker will pace the ventricle at a metronomic rate. However, in the presence of a sinus atrial rhythm, the VDD pacemaker will pace the ventricle in synchrony with the detected atrial rhythm.

The DVI mode A-V sequential pacemaker, as typified by U.S. Pat. No. 3,595,242 to Berkovits, provides for stimulation in both the atrium and ventricle while providing for ventricular sensing. In this form of pacemaker, a ventricular sense event initiates a V-A timer as well as a V-V timer. At the expiration of the V-A interval, the pacemaker generates an atrial pace event, and at the expiration of the V-V interval, the pacemaker generates a ventricular pace event. If a ventricular event occurs during the V-A or V-V time, the pacemaker is inhibited and recycled so that the V-A and V-V timer restart. This bifocal form of pacemaker preserves the hemodynamic advantages of sequential atrial and ventricular contractions.

The DDI mode pacer, as typified by U.S. Pat. No. 3,747,604 to Berkovits, includes a V-A and V-V timer and further includes an atrial sense amplifier for inhibiting the generation of an atrial pacing stimulus at the conclusion of the V-A interval if a naturally occurring atrial depolarization occurs within that time interval. This DDI mode of pacemaker, unlike the VAT or VDD pacemaker, does not resynchronize or restart the pacemaker's timer upon the sensing of arial events. Therefore, it does not provide the atrial tracking response exhibited by VAT and VDD devices.

Recently, dual sense-dual pace or DDD mode pacemakers, as typified by U.S. Pat. No. 4,312,355 to Funke, have been introduced to compensate for many of the disadvantages of the preceding forms of pacemakers and for providing more efficacious therapy in the event of an intermittent block during atrial pacing. The DDD pacemaker provides an atrial sense amplifier to generate an atrial sense signal that synchronizes the pacemaker by initiating an A-V timer. The A-V delay schedules the delivery of a ventricular pace event unless a ventricular sense event occurs within the A-V interval to inhibit or cancel the scheduled ventricular pace event. This form of pacemaker also provides a ventricular sense amplifier for initiating a V-A timer in response to a ventricular sense signal which schedules the generation of an atrial stimulus at the conclusion of the V-A interval unless an atrial sense event occurs to cancel the ventricular pace event within the A-V interval.

This prior art DDD form of pacemaker is represented by the state diagram of FIG. 2. Assuming that the machine is in the atrial observation state 24 (AOT), then an atrial sense event (AS) causes state transition 11 which causes the machine to enter the A-V delay state 12 where the A-V delay timer starts to time out an atrial-ventricular escape interval. If the A-V delay timer (AVD) times out (AVTO), then state transition 14 takes place moving the machine to the ventricular pacing state (VP)16. In this state, the machine delivers a pacing stimulus to the ventricle of the heart. At the conclusion of the pacing pulse, the machine moves via transition 18 to the refractory state 20 during which time the post ventricular-atrial refractory period (PVARP) is timed out. At the conclusion of the post ventricular-atrial refractory period (PVARP), the machine moves via transition 22 to the atrial observation state (AOT). In this state, the pacer is responsive to the atrial sense amplifier as previously described. If atrial activity is not sensed, then the machine will leave the atrial observation state as indicated by state transitiion 26 whereupon entering the atrial pacing state 28, the machine generates an atrial pacing stimulus. At the conclusion of the pacing pulse reflected by transitition 30, the machine re-enters the A-V delay state 12. If a ventricular sense event occurs during this state as indicated by state transition 32, the machine re-enters the refractory state 20.

This state machine description depicts the interaction of the pacer with the heart in response to the various cardiac events which may occur during the various timing cycles of the pacer.

Each of the previously discussed pacing modalities incorporates escape intervals defined as the time period extending from a sense event to the scheduled generation of a succeeding paced event, which are fixed at a discrete value during the operation of the pacer. Modern versions of each of these prior art pacemakers provide for the remote programming of such escape interval under the direction of a physician. However, once programmed, the intervals are not altered by pacemaker events.

Pacemakers have been proposed and built which alter the escape interval of the pacemaker in response to pacemaker detected cardiac events. An example of one such pacemaker is U.S. Pat. No. 4,052,991 to Zacouto as well as U.S. Pat. No. Re. 28,341 to Gobeli. The Zacouto machine is a ventricular pacemaker with ventricular sensing which alters the V-V escape interval of the pacemaker depending upon the timing of naturally occurring ventricular events. This pacemaker measures the time interval from a ventricular pace event to a subsequent ventricular sense event and sets the escape interval of the pacemaker to that value. In operation, a Zacouto orthorhythmic pacemaker has a nomimal V-V escape interval which results in the metronomic pacing of the ventricle at that rate in the absence of detected atrial ventricular activity. When a ventricular sense event occurs, the orthorhythmic pacemaker may provide an escape interval longer than the nominal escape interval which Zacouto refers to as negative hysteresis. Alternatively the pacer may provide for a shorter escape interval than the nominal value, which Zacouto refers to as positive hysteresis. Consequently, the orthorhythmic pacemaker represents a pacemaker in which the escape interval of the pacemaker is altered on a beat-to-beat basis in response to the detection of ventricular cardiac activity.

The Gobeli pacemaker is a VVI device that exhibits positive hysteresis under the nomenclature of Zacouto since the escape interval of the pacemaker is lengthened in response to a detected ventricular sense event.

More recently, pacers have been proposed which alter the stimulation escape interval based on the evoked QT time interval. See, for example, U.S. Pat. No. 4,228,803 to Rickards and No. 4,305,396 to Wittkampf et al.

BRIEF SUMMARY OF THE INVENTION

The pacemaker of the present invention shares many structures and functions with the previously described pacemakers. However, unlike prior art DDD pacers, this pacer's V-A interval (VAI) may vary in response to detected atrial activity. Additionally this pacer alters the pacing behavior or stimulation regime of the pacer depending on the temporal relationships between an atrial sense event and the preceding ventricular event. The objective of this pacemaker is to maintain physiologic cardiac contraction patterns over a wide frequency range and to achieve this goal in the presence of a wide variety of conduction faults and arrhythmias.

The functional characteristics of this pacemaker which permit the realization of these goals include the computation of an atrial stimulation back up rate (ASBU) which adapts the intervention frequency of the pacemaker to the observed spontaneous atrial rate; sense factor (SF) which governs the pacer's atrial synchronizing behavior; and intelligent P wave treatment at upper rate (IPTUR) which governs the pacer's action in the presence of competitive rhythms.

The feature denominated SF for sense factor is very desirable in instances where the patient exhibits intermittent atrial function due to disease processes such as sick sinus syndrome or atrial flutter. In the past, such patients would not be candidates for atrial synchronized pacers such as the DDD, but would be best served by a DVI pacer. This is an unfortunate result since many patients may be denied the benefit of atrial synchronized rate responsiveness because of occasional or transient atrial dysfunction. Sense factor addresses this problem by providing the physician with a parameter which can adapt the synchronizing response of the pacer to the disease condition. In operation, the atrial observation time (AOT) of the pacer is bifurcated into two intervals denominated T1 and T2. The ratio of these two times is the physician selected sense factor (T2/T1=SF). Atrial sense events which fall within T1 are not used to resynchronize the pacer yielding a DVI-like behavior, while atrial sense events falling within T2 resynchronize the pacer yielding a DDD-like behavior. Consequently SF permits the pacer to exhibit a smooth transition between DVI and DDD behavior dependent on the temporal relationship between the atrial sense event and its preceding ventricular event. This permits the benefit of atrially based physiologic stimulation to be brought to more patients. Conceptually T1 may be regarded as a post-ventricular atrial refractory period which is adjusted automatically based on the pacer's rate. However, unlike traditional refractory periods, the atrial sense amplifier is "on" and is sensing during this time period. Note that this T1 interval is long at low rates and short at higher rates. The physician can set a large T1 period via SF programming to prohibit or prevent a pacemaker mediated tachycardia without comprising the ability of the pacer to track the faster atrial rates.

The alert reader will recognize that the benefit conferred by SF, which is the ability of the patient's atria to dictate whether the pacer will follow the DDD or DVI regime, could extract a penalty in terms of rate variability. If one recalls that DVI pacing occur at a fixed lower rate and that DDD pacing occurs at the instantaneous atrial rate, then the ability to move from DDD to DVI and back again could result in large jumps in ventricular stimulation rates. ASBU, the atrial stimulation back-up rate, addresses this problem. This feature is described in excruciating detail later. For now it should be considered as a "flywheel" or the pacer's escape interval. The computation of the pacer's atrial escape interval contains "inertial" terms which ensure that the rate accelerates in a physiological sensible manner.

We now move to the behavior of the pacer at high rates. Once again the matter is described later in unrelenting detail, however, the IPTUR feature should be examined briefly to understand its relation to the schema. If a sequence of atrial sense events have fallen in T2, then the pacer's ASBU has been shortened to approximate the naturally observed Q-P or V-A time. When the pacer's rate and the heart's rate are similar, one runs the risk of competitive pacing. Competitive pacing occurs when a natural cardiac depolarization and a pacing stimulus occur together close in time. Let us assume that ASBU has scheduled an atrial stimulus 150 ms hence, and at present we sense a naturally occurring atrial event which has occurred in T1. IPTUR dictates that we cancel the scheduled atrial pace event even though it has landed in T1 and would at lower rates be ignored (DVI-like behavior). IPTUR, in essence, sets a window of inhibition which overrides the SF dictated response at higher rates.

BRIEF DESCRIPTION OF THE DRAWINGS

FIG. 1 is a timing diagram showing the relationships between intervals used to describe the invention.

FIG. 2 is a state diagram of a prior art DDD pacer.

FIGS. 3, 4 and 5 are hypothetical schematic timing diagrams depicting the pacer timing intervals and the simultaneous electrocardiographic recordings which show the interaction between the pacer and the heart.

FIG. 6 is a state diagram depicting the pacer of the present invention.

DESCRIPTION OF THE INVENTION

Figure 7:
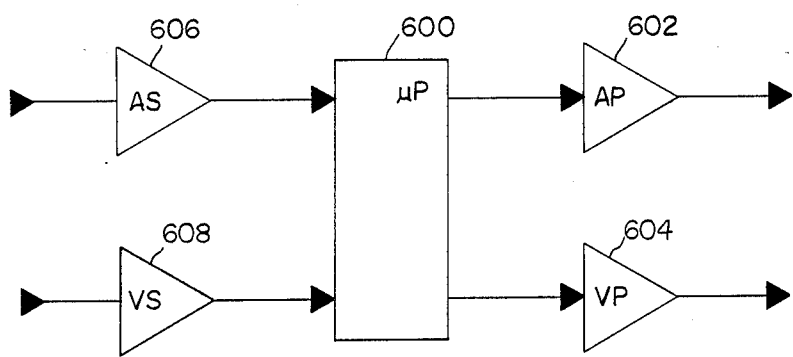
FIG. 7 is a functional block diagram of the pacemaker of the present invention.

Throughout the description, reference will be made to terms defined as follows:

VE is a ventricular event, either sense or pace;

VP is a ventricular pace event generated by the ventricular pulse generator.

VS is a venytricular sense event generated by the ventricular sense amplifier.

AP is an atrial pace event generated by the atrial pulse generator.

AS is an atrial sense event generated by the atrial sense amplifier.

$[VE \rightarrow AP]_n$ is the time interval from a ventricular event to the next scheduled AP event for the nth pacing cycle. This corresponds to the V-A escape interval of the pacer.

ASBU is the atrial stimulation back-up rate which corresponds to the V-A escape interval of the pacer. It comprises the arithmetic summation of two time intervals and is computed by the pacer in real time. [PVARP+AOT].

PVARP is the post ventricular atrial refractory period. The value is programmable. The total atrial refractory period is equal to the arithmetic sum of PVARP and the A-V delay interval of the pacer.

AOT is the atrial observation time. This period extends from the end of the PVARP to the end of the ASBU. [ASBU−PVARP]=AOT.

T1 is the first portion of the AOT.

T2 is the second portion of the AOT.

SF is the sense factor of the pacer and is the ratio of T2/T1. The value of SF is programmable and should vary from $10.0 > SF > 0.1$.

K1 is a programmable constant having a nominal value of 12 ms which is added to the nth value of $[VE \rightarrow AP]$ to generate the n+1 value of $[VE \rightarrow AP]$ or ASBU when an AS event occurs in T2.

K2 is a programmable constant having a nominal value of 50 ms which is added to the nth value of $[VE \rightarrow AP]$ to generate the n+1 value of $[VE \rightarrow AP]$ or ASBU when no AS events occur in the AOT.

K3 is a programmable constant having a nominal value of 150 ms. This time interval overlaps the last protion of T2 and ends with the AP event. Any AS event within the K3 portion of T2 is used to compute the next ASBU and is used to inhibit the impeding AP event. This provides protection from competitive pacing in the atrium.

As shown in connection with FIG. 1, the "V-A" or atrial escape interval of the pacemaker may be varied on a beat-to-beat basis. The atrial escape or VA interval is defined as the time from a ventricular event (VE) labeled 1 to the next atrial pace event (AP) olabeled 2 and may be expressed $[VE \rightarrow AP]_n$. This time interval $[VE \rightarrow AP]$ may be shortened for a subsequent pacing cycle $[VE \rightarrow AP]_{n+1}$ if an atrial event occurs within this time interval during a current pacing cycle. Similarly, the subsequent VA, atrial escape interval $[VE \rightarrow AP]_{n+1}$ of the pacemaker may be extended if no atrial activity is detected within the current interval. The atrial escape interval $[VE \rightarrow AP]_n$ is referred to as the atrial stimulation back-up interval. It may be recomputed on each beat, and it is abbreviated ASBU and labeled 3 in the figure. ASBU will vary between a preset maximum value and a preset minimum value. ASBU reflects the interval from a ventricular event to the next scheduled atrial pace event for any given pacing cycle.

In a DDD mode pacemaker, the atrial refractory period is extended beyond ventricular events. Consequently, the pacer exhibits a post ventricular atrial refractory period (PVARP) labeled 4 in the figure, which renders the pacer refractory or insensitive to atrial depolarizations occurring within this fixed time after the ventricular event, depicted by atrial sense event 8 in the figure. In most DDD pacers, this PVARP is a programmed parameter. In a conventional DDD pacer, the conclusion of the PVARP starts a time window during which the pacer can sense atrial events. For our purposes, we define the time period starting with the end of the atrial refractory period to the time out of the ASBU interval as the atrial observation time, abbreviated AOT and labeled 5 in the figure.

In the present invention, the AOT is bifurcated into a first sensing period T1 labeled 6 and a second sensing period T2 labeled 7 where AOT=T1+T2. The ratio of time intervals T2/T1 is named SF for sense factor. The sense factor may range from 0.1 10.0 and is a physician programmable parameter, $10.0 > SF > 0.1$.

The maximum value of ASBU is defined by physician selection of the lower pacing rate for the pacemaker while the minimum value for ASBU is comparable to the duration of the post ventricular atrial refractory period which is defined by the physician when he selects the atrial refractory period.

In operation, ASBU is shortened when an atrial sense event occurs in T2 depicted by atrial sense event 9 in FIG. 1. In this instance, the pacer shortens the atrial escape interval so that it just exceeds the observed atrial rate by a small amount. In this instance, the value of ASBU is set equal to the time period from the ventricular event ot the atrial sense event with the addition of a small increment of positive hysteresis K1, $ASBU_{n+1} = [VE \rightarrow AS]_n + K1$, where the value of K1 is on the order of 12 ms and is programmable.

Consequently, an atrial sense event in the T2 portion of the atrial observation time (AOT) can accelerate the pacer through the ASBU calculation. Additionally this atrial sense event during T2 resynchronizes the pacer by starting the A-V delay timer and also inhibits the otherwise scheduled atrial pace event.

Clearly atrial sense events can also occur during the T1 portion of the atrial observation time as depicted in the figure by atrial sense event 10. The pacer does not use atrial sense events during T1 to update the ASBU value. Atrial events sensed during T1 may or may not be used to inhibit the scheduled atrial pace event depending on the temporal proximity between the atrial sense and the scheduled atrial pace events. If the time from the As event to the AP event is less than a constant K3, then the scheduled AP even is cancelled [AS→AP-]<K3, and the pacer exhibits an atrial inhibited response. If, however, the time from the As event to the AP exceeds K3, then the pacer will not cancel the AP event and will not exhibit an atrial inhibited behavior.

In the alternative, a cardiac cycle may transpire wherein no atrial sense event occurs. In this case, the value of ASBU is lengthened gradually. In this instance the n+1 value of ASBU is set equal to the preceeding n value with the addition of a fallback interval K2; $ASBU_{n+1} = ASBU_n + K2$. The value of K2 is in the order of 50 ms and is programmable.

In conclusion, it should be observed that ASBU may be shortened or accelerated by rapidly recurring atrial activity, and ASBU will be lengthened by either the absence of atrial activity or the occurrence of atrial activity early in the cardiac cycle.

FIGS. 3, 4 and 5 shown schematic representations for a pacemaker according to the present invention. In each figure, a schematic EKG trace is shown in conjunction with the various pacemaker time intervals to depict the interaction of the pacemaker with the heart.

Turning to FIG. 3, cardiac pacing cycle A shows the sequential stimulation of both chambers of the patient's heart at the programmed lower rate limit (LR). The electrogram begins with a spontaneously occurring R-wave at 49 which gives rise to a ventricular sense event at 50, initiating the post ventricular atrial refractory period of the pacemaker shown at 52. At the conclusion of the atrial refractory period, the pacemaker enters the atrial observation time. The first portion of the atrial observation time is labeled T1 in the diagram and begins at 54. At the conclusion of the first portion of the observation time, the second portion of the observation time begins at 56. As shown in FIG. 3, no atrial sense events occur within the atrial observation time. Therefore, at the conclusion of this time period, the pacemaker emits an atrial pacing pulse at 58, depicted as the pacing artifact 59 preceding atrial complex or P-wave 61.

This time interval from a ventricular event 50 to the subsequent generation of an atrial pacing event 58 is referred to as the atrial escape interval of the pacemaker and is referred to as the atrial stimulation back-up interval or ASBU. Complex A shows a pacemaker which has a programmed post ventricular-atrial refractory period of 200 ms with a V-A excape interval programmed to 600 ms. The sense factor of this pacemaker has been set at 1 thus bifurcating the atrial observation time which is defined as the time period from the conclusion of the atrial refractory period to the generation of the atrial pacing event 58 into two equal time intervals T1 and T2. Complex A represents the maximum value for ASBU for the programmed settings enumerated above.

After the generation of the atrial pacing event 58, the A-V delay timer of the pacemaker begins timing out the A-V interval shown as 60 in FIG. 3. At the conclusion of this interval, a ventricular pacing event 62 is generated since no ventricular sensed activity was detected by the pacemaker within the A-V interval. The ventricular pace event 62 gives rise to the pacing artifact 63 shown on the schematic EKG prior to the stimulated R-wave 64.

The ventricular event 62 once again starts the post ventricular atrial refractory period timer at 66. At the conclusion of the atrial refractory period, the atrial observation time begins at 68. During the first portion T1 of the atrial observation time, an atrial sense event occurs at 70. This is shown in the schematic EKG as P-wave 72. This P-wave, since it falls within T1, does not give rise to a new value for ASBU nor does not inhibit the scheduled atrial pace event for the cardiac cycle shown in B in FIG. 3, nor does it initiate the A-V timer. In this particular instance, the pacemaker treats atrial event 70 as if it fell within an atrial refractory period.

Once again, at the conclusion of the atrial observation time at 72. the pacemaker generates an atrial pace event 74 giving rise to a pacing artifact shown on the schematic EKG at 73 preceding P-wave 75.

The atrial pace event at 74 initiates the A-V delay timer resulting in the generation of a ventricular pacing pulse 76 at the conclusion of the A-V delay time and shown on the schematic EKG as pacing artifact 77 preceding the stimulated R-wave 78. At this point, the pacemaker enters the cardiac cycle C in FIG. 3. The computed atrial stimulation back-up rate for this cardiac cycle is 600 ms based upon the information shown within the preceding cardiac cycles A and B. During this cardiac cycle, however, an atrial sense event 80 occurs during the latter portion of the atrial observation time falling within T2. The atrial sense event 80 truncates the remaining portion of T2 and starts the A-V delay timer at 84. Since no naturally conducted R-wave follows P-wave 86, the A-V delay timer times out at 88 generating the ventricular pacing artifact 87 preceding ventricular complex 89.

In pacing cycle D, the occurrence of the atrial sense event 80 during the atrial observation time has accelerated the pacemaker by shortening the atrial escape interval.

ASBU for cardiac cycle D is 510 ms. This value is computed by adding a small hysteresis increment of 10 ms to the observed [VP→AS] time interval of 500 ms of cardiac cycle C. The sense factor (SF) remains constant at 1 thus bifurcating the 310 ms atrial observation time into equal 155 ms sense windows T1, T2.

During cardiac cycle D no atrial events are detected. Therefore, the pacemaker provides the atrial pacing event 90 at the conclusion of the atrial observation time giving rise to the pacing artifact 91 preceding the provoked P-wave 92 on the EKG. At the conclusion of the A-V delay, the pacemaker generates a ventricula4 pace event 94 giving rise to the pacing artifact 95 preceding stimulated R-wave 97.

Since there has been no detected atrial activity during cardiac cycle D, the value of ASBU is incremented for cardiac cycle E. A fallback increment K2 is added to the value of ASBU. The fallback increment K2 may vary between 10 and 100 ms and has a nominal value of 50 ms giving rise to the ASBU for cardiac cycle E of 560 ms.

Although the fallback increment may be made a constant, it is also contemplated that this value may be logically coupled to the SF value selected by the physician. In general, large values of SF would correspond to large values of K2, and low SF values would map to small values of K2.

With respect to FIG. 3, the computation of the atrial stimulation back-up interval has been shown. The pacemaker's atrial escape interval was accelerated by atrial event 80 and was extended in the absence of atrial activity as shown in connection with cardiac cycle E.

In operation, the value of ASBU may vary from a maximum imposed by the lower rate programmed by the physician as depicted in cardiac cycles A and B up to a minimum value dictated by the duration of the PVARP.

The operation of the pacemaker at high atrial rates and at various sense factors is shown in connection with FIGS. 4 and 5.

Turning to FIG. 4, the lower rate of the pacemaker has remained programmed to the 600 ms value, and the PVARP has remained at 200 ms. In the figure, however, the sense factor has been changed from 1 to 0.25, yielding a larger T1 portion of the atrial observation time.

In the figure, pacing cycle J begins with spontaneous R-wave 400 which gives rise to ventricular sense event 402 initiating the post ventricular atrial refractory period at 404. At the conclusion of the PVARP, the atrial observation time begins. In this example, the SF is 0.33.

The absence of atrial activity during the AOT results in the scheduled stimulation of the atria at 410, the conclusion of the atrial observation time is depicted by pacing artifact 412 preceding P-wave 414. This atrial pace event 410 starts the A-V delay time of the pacer at 418. At the conclusion of the A-V delay time, a ventricular pace event 420 is generated as illustrated by pacing artifact 422 preceding R-wave 424.

The events of pacing cycle M are identical to pacing cycle J. Pacing cycles K and L are similar to pacing cycles J and M except that atrial activity occurs during cycles K and L.

In pacing cycle K, the atrial sense event occurs at 426 within the T1 portion 428 of the atrial observation time. The pacer computes the time interval remaining until the next scheduled atrial pace event 430. This time interval [AS→AP] is compared with a physician programmable constant K3. Then the pacer effectively ignores the atrial sense event in the sense that the machine remains in the atrial observation state. When the computed interval is shorter than K3, the pacer will inhibit the scheduled atrial pace event as more fully described in connection with pacing cycle H.

Note that ASBU for each pacing cycle in FIG. 4 has remained constant. This occurs in the example of FIG. 4 because atrial events in T1 do not accelerate the pacer by shortening ASBU, and the increment K2 which may be added to ASBU after each cycle cannot extend the value of ASBU below the lower programmed state.

FIG. 5 is similar to FIG. 4 in that all programmable values are the same save sense factor which has a value of 0.25 in FIG. 5. Also, the occurrence of atrial event being the same between FIGS. 4 and 5.

Turning to FIG. 5, note that due to the change in SF, the atrial sense event 500 has occurred during the first few milliseconds of the T2 portion 502 of the atrial observation time.

In response to As 500, the pacer enters the A-V delay state wherein the programmed A-V delay is timed out. At the conclusion of this A-V delay 504, a ventricular pace event 506 is generated completing pacing cycle F.

ASBU for pacing cycle G is calculated based on the occurrence of AS 500. The pacer sets ASBU for pacing cycle G equal to the observed time interval from the ventricular event 501 to the atrial sense event 500 of 310 ms with the addition of an increment K1 of 10 ms. Therefore, the value of ASBU for pacing cycle G is 320 ms with an AOT value of 120 ms. Since no atrial sense events occur during pacing cycle G, the ASBU for pacing cycle H is incremented by K2=50 ms yielding an ASBU of 370 ms; AOT=170 ms; T1=42.5 ms and T2=127.5 ms.

During T1 of cycle H, an atrial sense event occurs 508. The pacer once again computes the time to the next atrial pace event which in this case is approximately 120 ms. [AS→AP]>130 ms. In the example, we assume a value of K3 of 150 ms and note that [AS→AP] 150 ms. This illustrates that while operating near the upper rate limit the duration of T1 and T2 may be quite short which reduces the likelihood that all P-waves will be sensed within T2. In the illustration, the naturally occurring atrial event 508 occurs so close to the scheduled atrial pace event that there is a likelihood that the scheduled AP event would fall within the repolarization or vulnerable time of the atrial and thus compete with the natural atrial rhythm. To avoid this, possibly the pacer inhibits atrial pace events which would occur less than a preset time, i.e. K3 prior to the atrial stimulation time.

The state machine depicted in FIG. 6 describes the differences between the pacer according to the present invention and the pacer disclosed in U.S. Pat. No. 4,312,355.

At the conclusion of the post ventricular atrial refractory, the pacer enters the atrial observation state 200 via state transition atrial refractory. The pacer enters the atrial observation state 200 via state transition 202. The atrial observation time (AOT) is bifurcated by the sense factor (SF), and the total duration of the T1 and T2 segments depends on the SF as well as the observed atrial sensing rate. If an atrial sense event occurs during T1 and the computed time period from the atrial sense event AS to the end of the AOT exceeds the value of K3, then the pacer remains in AOT state depicted by loop 204. In this situation, the machine effectively ignores the detected atrial event. If, however, the AS event in T1 gives rise to a value of [AS→AP] which is smaller than K3, then the pacer will inhibit the otherwise scheduled atrial pace event AP and move to the A-V delay state 206 (AVD) at the conclusion of the atrial observation time (AOT). This is shown by state transition 205.

Another path for leaving the AOT state 200 is shown by state transition 208. In this instance, there has been no atrial sense event AS, and the atrial observation time has expired at the end of T2. The machine then enters the atrial pace state 209 where the pacer generates an atrial stimulus on the atrial lead.

As illustrated in FIG. 7, the machine herein described has been reduced to practice through the use of a commercially available Commodore PET personal computer 600 coupled to conventional pacer atrial sense amplifier 602, ventricular sense amplifier 604, atrial output stimulus generator 606, and ventricular output stimulus generator 608. All timing functions are performed by computer 600. An annotated software listing written in 6502 ASSEMBLER CODE is reproduced as follows:

```
100   rem *** ddd-pacemaker with gliding atrial
      refractory ***
105   rem *** vsap and intelligent p wave treatment
      (ipt) ***
110   rem *** basref15+masref15 h.d.funke aug. 14,
      1983 ***
115   rem *** ipt-time 20494,x * ipt off 20529,0 * ipt on
      20529,251 ***
120   rem *** d00 20020,0 * 20029,0 * 20070,0 *
      20202,0 ***
125   poke59468,14:poke59459,67
130   print"     Please wait, I'm loading":
      print:print
135   print"     the machine program!"
140   fori=39645to40197:pokei-19645,peek(i):nexti
145   lr$="70":av$="180":hy$="25":sf$=".3":hr$="120":
      wa$=".5":wv$=".5":mo$="1"
150   print"     *** DDD-Autoref-Pacemaker ***":print:
      print:goto160
155   print "  "
160   bl=40:re=150:cali=115:w7=30
165   print"  Lo Rate ( 50-120 PPM) ?";tab(32);lr$;
170   ifr=0thenprint" ":goto180
175   print"     ";tab(30);:inputlr$:print
180   lr=val (lr$):iflr<50orlr>120thenprint"     ":gotto165
185   print"  AV Time ( 20-250 ms) ?";tab(32);av$;
190   ifr=0thenprint"     ":goto200
195   print"     ";tab(30);:inputav$:print
200   av=val (av$):ifav<20orav>250thenprint"     ":goto165
205   print" AV Hyst ( 00-100 ms) ?";tab(32);hy$;
210   ifr=0thenprint"     ":goto220
215   print"     ";tab(30);:inputhy$:print
220   hy=val(hy$):ifhy>av-20orhy>100thenprint"     ":goto205
225   print" Sense Fact ( 0.1-1.0 ) ?";tab(32);sf$;
230   ifr=0thenprint"     ":goto240
235   print"     ";tab(30);:inputsf$:print
240   sf=val(sf$):ifsf<.1orsf>1thenprint"     ":goto225
245   mr=int(60000/(av+re+20))
250   print"  Hi Rate (";int(lr+1);:iflr+>99.9thenprint
      "   ";
255   ifint(lr+1)<100thenpoke33745,32
260   print"- ";int(mr);tab(23);"PPM) ?";tab(32);hr$;
265   ifr=0thenprint"     ":goto275
270   print"     ";tab(30);:inputhr$:print
275   hr=val(hr$):ifhr<lr+1orhr>mrthenprint"     ":goto250
280   print"  PWA    ( 00-2.0 ms) ?";tab(32);wa$;
285   ifr=0thenprint"     ":goto295
290   print"     ";tab(30);:inputwa$:print
295   wa=val(wa$):ifwa>2thenprint"     ":goto280
300   print"  PWV    ( 00-2.0 ms) ?";tab(32);wv$;
305   ifr=0thenprint"     ":goto315
310   print"     ";tab(30);:inputwv$:print
315   wv=val(wv$):ifwv>2thenprint"     ":goto300
320   print"  DDD(1), DVI(2), VVI(3) ?";tab(32);mo$;
325   ifr=0thenprint"     ":goto335
330   print"     ";tab(30);:inputmo$:print
335   mo=val(mo$):ifmo<>1andmo<>2andmo<>3thenprint"     ":
      goto320
340   print:print"  New entries: press any key."
345   print"  New start: run 145":r=1
350   rem *** lr, av, hy, sf, hr, bl, re, wa, wv, cali,
      w7 ***
355   av=int(av/4):hy=int(hy/4):bl=int(bl/4):re=int(re/4):
      w7=int(w7/4)
360   wa=int(wa*115):wv=int(wv*115)
365   poke20128,bl:poke20251,re:poke20106,wa:poke20229,wv
370   poke20010,ca:poke20060,ca:poke20133,ca
375   poke20183,ca:poke20256,ca:poke20306,ca
380   poke20104,254:ifwa=0thenpoke20104,255:poke20106,1
385   poke20227,253:ifwv=0thenpoke20227,255:poke20229,1
390   ifmo=1thenpoke20070,251:poke20104,254:ifwa=0thenpoke
      20104,255
395   ifmo=2thenpoke20070,0:poke20104,254:ifwa=0thenpoke
      20104,255
400   ifmo=3thenpoke20070,0:poke20104,255
405   w4=av-bl-w7:w6=av-hy-w7:ws=int(15000/lr)-av-re:rem
      ws=w1+w2
410   w1=int(ws/(sf+1)):w2=ws-w1:tm=int(15000/hr)-re-w6-w7
415   rem *** w1, w2, bl, w4, re, w6, tm, w7 ***
420   ifw1<1thenw1=1
```

-continued

| | | | |
|---|---|---|---|
| 425 | ifw2<1thenw2=1 | | |
| 430 | ifw4<1thenw4=1 | | |
| 435 | ifw6<1thenw6=1 | | |
| 440 | iftm<1thentm=1 | | |
| 445 | poke20370,tm:poke20390,tm:poke20410,tm:poke20429,w7 | | |
| 450 | poke20353,w1:poke20005,tm:poke20055,w2:poke20178,w4: poke 20301,w6 | | |
| 455 | sys20004:geta$:ifa$<>""thengoto155 | | |
| 460 | poke20055,int(peek(20005)*sf):ifpeek(20005)< tmthenpoke20005,tm | | |
| 465 | goto455 | | |
| ready. | | | |
| 20000 | rts | | |
| 20001 | nop | | |
| 20002 | brk | | |
| 20003 | brk | | |
| 20004 | lda | 50 | |
| 20006 | stam | 20002 | |
| 20009 | lda | 115 | |
| 20011 | stam | 20003 | WAIT P.R. |
| 20014 | ldam | 59471 | |
| 20017 | ora | 251 | |
| 20019 | cmp | 251 | |
| 20021 | beq | 20045 | |
| 20023 | ldam | 59471 | |
| 20026 | ora | 247 | |
| 20028 | cmp | 247 | |
| 20030 | beq | 20048 | |
| 20032 | decm | 20003 | |
| 20035 | bne | 20014 | |
| 20037 | decm | 20002 | |
| 20040 | bne | 20009 | |
| 20042 | jmp | 20528 | |
| 20045 | jmp | 20476 | |
| 20048 | jmp | 20250 | - refract. |
| 20051 | nop | | |
| 20052 | orap | 87 | |
| 20054 | lda | 14 | |
| 20056 | stam | 20052 | |
| 20059 | lda | 115 | |
| 20061 | stam | 20053 | |
| 20064 | ldam | 59471 | |
| 20067 | ora | 251 | |
| 20069 | cmp | 251 | WAIT P.R. |
| 20071 | beq | 20095 | |
| 20073 | ldam | 59471 | |
| 20076 | ora | 247 | |
| 20078 | cmp | 247 | |
| 20080 | beq | 20098 | |
| 20082 | decm | 20053 | |
| 20085 | bne | 20064 | |
| 20087 | decm | 20052 | |
| 20090 | bne | 20059 | |
| 20092 | jmp | 20102 | |
| 20095 | jmp | 20365 | - atrial stim. rate back-up (ASBU) |
| 20098 | jmp | 20250 | - refract |
| 20101 | nop | | |
| 20102 | sei | | |
| 20103 | lda | 254 | |
| 20105 | ldx | 57 | |
| 20107 | stam | 59471 | |
| 20110 | dex | | |
| 20111 | nop | | |
| 20112 | nop | | STIM A |
| 20113 | nbe | 20110 | |
| 20115 | ldx | 255 | |
| 20117 | stym | 59471 | |
| 20120 | cli | | |
| 20121 | jmp | 20348 | - SLOW DOWN |
| 20124 | nop | | |
| 20125 | brk | | |
| 20126 | brk | | |
| 20127 | lda | 10 | |
| 20129 | stam | 20125 | |
| 20132 | lda | 115 | |
| 20134 | stam | 20126 | |
| 20137 | ldam | 59471 | |
| 20140 | ora | 251 | WAIT BLANKING |
| 20142 | cmp | 0 | |
| 20144 | beq | 20168 | |
| 20146 | ldam | 59471 | |
| 20149 | ora | 247 | |

-continued

| | | | | |
|---|---|---|---|---|
| 20151 | cmp | 0 | | |
| 20153 | beq | 20171 | | |
| 20155 | decm | 20126 | | |
| 20158 | bne | 20137 | | |
| 20160 | decm | 20125 | | |
| 20163 | bne | 20132 | | |
| 20165 | jmp | 20177 | | |
| 20168 | jmp | 0 | | |
| 20171 | jmp | 0 | | |
| 20174 | nop | | | |
| 20175 | brk | | | |
| 20176 | brk | | | |
| 20177 | lda | 28 | | |
| 20179 | stam | 20175 | | |
| 20182 | lda | 115 | | |
| 20184 | stam | 20176 | | |
| 20187 | ldam | 59471 | | |
| 20190 | ora | 251 | | |
| 20192 | cmp | 0 | WAIT | |
| 20194 | beq | 20218 | REFRACT. | |
| 20196 | ldam | 59471 | | |
| 20199 | ora | 247 | | |
| 20201 | cmp | 247 | | |
| 20203 | beq | 20221 | | |
| 20205 | decm | 20176 | | |
| 20208 | bne | 20187 | | |
| 20210 | decm | 20175 | | |
| 20213 | bne | 20182 | | |
| 20215 | jmp | 20428 | - Wait R for R-inhib??? without VSAP | |
| 20218 | jmp | 0 | | |
| 20221 | jmp | 20385 | - VSAP | |
| 20224 | nop | | | |
| 20225 | sei | | | |
| 20226 | lda | 253 | | |
| 20228 | ldx | 57 | | |
| 20230 | stam | 59471 | STIM. V | |
| 20233 | dex | | | |
| 20234 | nop | | | |
| 20235 | nop | | | |
| 20236 | bne | 20233 | | |
| 20238 | ldx | 255 | | |
| 20240 | stxm | 59471 | | |
| 20243 | cli | | | |
| 20244 | jmp | 20250 | - Refract. | |
| 20247 | nop | | | |
| 20248 | brk | | | |
| 20249 | brk | | | |
| 20250 | lda | 37 | | |
| 20252 | stam | 20248 | | |
| 20255 | lda | 115 | | |
| 20257 | stam | 20249 | | |
| 20260 | ldam | 59471 | WAIT REFRACT. | |
| 20263 | ora | 251 | | |
| 20265 | cmp | 0 | | |
| 20267 | beq | 20291 | | |
| 20269 | ldam | 59471 | | |
| 20272 | ora | 247 | | |
| 20274 | cmp | 0 | | |
| 20276 | beq | 20294 | | |
| 20278 | decm | 20249 | | |
| 20281 | bne | 20260 | | |
| 20283 | decm | 20248 | | |
| 20286 | bne | 20255 | | |
| 20288 | jmp | 20538 | | |
| 20291 | jmp | 0 | | |
| 20294 | jmp | 0 | | |
| 20297 | nop | | | |
| 20298 | brk | | | |
| 20299 | brk | | | |
| 20300 | lda | 32 | | |
| 20302 | stam | 20298 | | |
| 20305 | lda | 115 | | |
| 20307 | stam | 20299 | | |
| 20310 | ldam | 59471 | | |
| 20313 | ora | 251 | WAIT R | |
| 20315 | cmp | 0 | (after atrial sense) | |
| 20317 | beq | 20341 | VSAP - DECIMAL? | |
| 20319 | ldam | 59471 | | |
| 20322 | ora | 247 | | |
| 20324 | cmp | 247 | | |
| 20326 | beq | 20344 | | |
| 20328 | decm | 20299 | | |

-continued

| | | | | |
|---|---|---|---|---|
| 20331 | bne | 20310 | | |
| 20333 | decm | 20298 | | |
| 20336 | bne | 20305 | | |
| 20338 | jmp | 20428 | - Wait R for R-in???? witout VSAP | |
| 20341 | jmp | 0 | | |
| 20344 | jmp | 20405 | - VSAP | |
| 20347 | nop | | | |
| 20348 | clc | | | |
| 20349 | ldam | 20005 | | |
| 20352 | cmp | 101 | - Lowest rate needed | SLOW DOWN |
| 20354 | bcs | 20361 | | |
| 20356 | adc | 2 | - Slow down by 2×4=8ms | AFTER |
| 20358 | stam | 20005 | | |
| 20361 | jmp | 20127 | - Blanking | ATRIAL STIM |
| 20364 | nop | | | |
| 20365 | sec | | | |
| 20366 | ldam | 20005 | | |
| 20369 | cmp | 49 | | |
| 20371 | bcc | 20381 | | |
| 20373 | sbcm | 20052 | - This time from wait P.R. elapse | |
| 20376 | adc | 5 | - Soothing rate changes | ASBU |
| 20378 | stam | 20005 | - Store new time back | |
| 20381 | jmp | 20300 | - Wait R | |
| 20384 | tax | | | |
| 20385 | sec | | | |
| 20386 | ldam | 20005 | | |
| 20389 | cmp | 49 | - Control for already existing maximal rate | |
| 20391 | bcc | 20401 | | VSAP |
| 20393 | sbcm | 20175 | - This time from wait R could not elapse because of early R. | AFTER ATRIAL STIM |
| 20396 | sbc | 4 | | |
| 20398 | stam | 20005 | - Time for acceleration stored back | |
| 20401 | jmp | 20250 | - Refract. | |
| 20404 | tax | | | |
| 20405 | sec | | | |
| 20406 | ldam | 20005 | | |
| 20409 | cmp | 49 | - Max rate checking required? | |
| 20411 | bcc | 20421 | | VSAP |
| 20413 | sbcm | 20298 | - This time could not elapse because of early R. | AFTER ATRIAL SENSE |
| 20416 | sbc | 4 | | |
| 20418 | stam | 20005 | - Later time stored back | |
| 20421 | jmp | 20250 | - Refract. | |
| 20424 | tax | | | |
| 20425 | nop | | | |
| 20426 | brk | | | |
| 20427 | brk | | | |
| 20428 | lda | 7 | | |
| 20430 | stam | 20426 | | |
| 20433 | lda | 125 | WAIT R | |
| 20435 | stam | 20427 | (for R-inhibition) | |
| 20438 | ldam | 59471 | (if R, no VSAP) | |
| 20441 | ora | 251 | | |
| 20443 | cmp | 0 | | |
| 20445 | beq | 20469 | | |
| 20447 | ldam | 59471 | | |
| 20450 | ora | 247 | | |
| 20452 | cmp | 247 | | |
| 20454 | beq | 20472 | | |
| 20456 | decm | 20427 | | |
| 20459 | bne | 20438 | | |
| 20461 | decm | 20426 | | |
| 20464 | bne | 20433 | | |
| 20466 | jmp | 20225 | - Stim R. | |
| 20469 | jmp | 0 | | |
| 20472 | jmp | 20250 | - Refractory | |
| 20475 | tax | | | |
| 20476 | tax | | | |
| 20477 | tax | | | |
| 20478 | tax | | | |
| 20479 | tax | | | |
| 20480 | lda | | | |
| 20482 | stam | 20020 | | |
| 20485 | nop | | | |
| 20486 | ldam | 20002 | | |
| 20489 | adcm | 20055 | | |
| 20492 | nop | | | |
| 20493 | cmp | 60 | - 1PT-Time | |
| 20495 | bcs | 20513 | | |

-continued

| | | |
|---|---|---|
| 20497 | nop | |
| 20498 | lda | 79 |
| 20500 | stam | 20094 |
| 20503 | lda | 124 |
| 20505 | stam | 20093 |
| 20508 | jmp | 20023 |
| 20511 | nop | |
| 20512 | nop | |
| 20513 | lda | 78 |
| 20515 | stam | 20094 |
| 20518 | lda | 134 |
| 20520 | stam | 20093 |
| 20523 | jmp | 20023 |
| 20526 | tax | |
| 20527 | tax | |
| 20528 | lda | 251 |
| 20530 | stam | 20020 |
| 20533 | jmp | 20054 |
| 20536 | tax | |
| 20537 | tax | |
| 20538 | lda | 78 |
| 20540 | stam | 20094 |
| 20543 | lda | 134 |
| 20545 | stam | 20093 |
| 20548 | jmp | 20000 |
| 20551 | tax | |
| 20552 | tax | |

What is claimed is:

1. In a pacemaker of the type having:
    (a) an atrial sense amplifier for producing atrial sense event signals (AS) in response to atrial depolarizations;
    (b) a ventricular sense amplifier for producing ventricular sense event signals (VS) in response to ventricular depolarizations;
    (c) an atrial pulse generator for producing atrial stimulating pulses in response to atrial pace event signals (AP);
    (d) a ventricular pulse generator for producing ventricular stimulating pulses in response to ventricular pace event signals (VP);
    (e) timing means for timing V-A escape intervals and for generating said atrial pace event signals at the conclusion of said V-A escape intervals and for timing A-V escape intervals and for generating said ventricular pace event signals at the conclusion of said A-V escape intervals, said V-A escape intervals initiated by the occurrence of said ventricular pace event signals or said ventricular sense event signals, said A-V escape intervals initiated by the occurrence of said atrial sense event signals or said atrial pace event signals, the improvement wherein;
    (f) said timing means includes means for dividing each said V-A escape interval into a first time interval and a subsequent second time interval, said timing means initiating timing of said A-V escape intervals in response to the occurrence of said atrial sense events during one of said second time intervals, but not in response to the occurrence of a said atrial sense event signal during one of said first time intervals, said timing means including means responsive to one of said atrial sense event signals occurring within one of said second time intervals to decrease the duration of a subsequent one of said V-A escape intervals and the duration of said first time interval therein.

2. A pacemaker according to claim 1 wherein said timing means is further responsive to the absence of said atrial sense event signals occurring within one of said second time intervals to increase the duration of a subsequent one of said V-A escape intervals and the said first time interval therein.

3. A pacemaker according to claim 1 or claim 2 wherein said timing means further comprises means for defining an inhibition interval beginning a predetermined time before the expiration of each said V-A escape interval, said timing means responsive to the occurrence of one of said atrial sense event signals which occurs in both the said first time interval and the said inhibition interval during one of said V-A escape intervals for preventing the generation of an atrial stimulating pulse at the expiration of said one of said V-A time intervals and for initiating timing of a said A-V escape interval at the expiration of said one of said V-A escape intervals.

4. A pacemaker according to claim 1 wherein said means responsive to one of said atrial sense events occurring within one of said second time intervals to decrease the duration of a subsequent one of said V-A escape intervals comprises means for measuring the time between the occurrence of said one of said atrial sense event signals and the immediately previous ventricular pace event signal and means for setting the duration of said subsequent one of said V-A escape intervals as a function of the measurement performed by said measuring means.

5. In a pacemaker of the type having:
    (a) an atrial sense amplifier for producing atrial sense event signals (AS) in response to atrial depolarizations;
    (b) a ventricular sense amplifier for producing ventricular sense event signals (VS) in response to ventricular depolarizations;
    (c) an atrial pulse generator for producing atrial stimulating pulses in response to atrial pace event signals (AP);
    (d) a ventricular pulse generator for producing ventricular stimulating pulses in response to ventricular pace event signals (VP); and
    (e) timing means for timing V-A escape intervals and for generating atrial pace event signals at the conclusion of said V-A escape intervals and for timing A-V escape intervals and for generating ventricular pace event signals at the conclusion of said A-V escape intervals, said V-A escape intervals initiated with the occurrence of said ventricular sense event signals or said ventricular pace event signals, said A-V escape intervals initiated with the occurrence of said atrial sense event signals or said atrial pace event signals, the improvement wherein;

(f) said timing means further comprises means for dividing each said V-A escape interval into a first time interval and a subsequent second time interval, said timing means initiating timing of said A-V intervals in response to said atrial sense event signals occurring during said second time intervals, but not in response to said atrial sense event signals occurring during said first time intervals, said timing means further comprising means responsive to the occurrence of one of said atrial sense event signals during one of said second time intervals for decreasing the duration of a subsequent one of said first time intervals in a subsequent one of said V-A escape intervals.

6. A pacemaker according to claim 5 wherein said timing means further comprises means responsive to the absence of said atrial sense event signals occurring within one of said second time intervals to increase the duration of a subsequent one of said first time intervals in a subsequent one of said V-A escape intervals.

7. A pacemaker according to claim 5 or claim 6 wherein said timing means further comprises means for defining an inhibition interval beginning a predetermined time prior to the expiration of each said V-A escape interval and wherein said timing means includes means responsive to the occurrence of one of said atrial sense event signals which occurs during both the said first time interval and the said inhibition interval during one of said V-A escape intervals for preventing generating of an atrial pace event signal at the conclusion of said one of said V-A escape intervals and for initiating timing of said A-V escape interval at the expiration of said one of said V-A escape intervals.

8. A pacemaker according to claim 1 or claim 5 wherein said means for dividing each said V-A escape interval into a first time interval and a second time interval comprises means for adjusting the durations of said first time interval and said second time interval such that the proportional relationship (SF) of the durations of said first and second time intervals remains constant from one of said V-A escape intervals to the next of said V-A escape intervals.

9. In a pacemaker of the type having:
(a) an atrial sense amplifier for producing atrial sense event signals (AS) in response to atrial depolarizations;
(b) a ventricular pulse generator for producing ventricular stimulating pulses in response to ventricular pace event signals (VP);
(c) timing means for timing A-V escape intervals following the occurrence of said atrial sense event signals and for generating said ventricular pace event signals at the conclusion of said A-V escape intervals, the improvement wherein;
(d) said timing means further comprises means for determining first time intervals following said ventricular pace event signals and second time intervals following said first time intervals, said timing means initiating the timing of said A-V escape intervals in response to said atrial sense event signals occurring during said second time intervals, but not in response to said atrial sense event signals occurring during said first time intervals, said timing means further comprising means responsive to the occurrence of one of said atrial sense event signals within one of said second time intervals for decreasing the duration of a subsequent one of said first time intervals.

10. A pacemaker according to claim 9 wherein said timing means further comprises means responsive to the absence of said atrial sense event signals occurring within one of said second time intervals to increase the duration of a subsequent one of said first time intervals.

11. A pacemaker according to claim 5 or claim 9 wherein said means responsive to the occurrence of one of said atrial sense event signals during one of said second time intervals for decreasing the duration of a subsequent one of said first time intervals further comprises measuring means for measuring the time between the occurrence of said one of said atrial sense event signals and the immediately preceding one of said ventricular pace event signals, said timing means further comprising means for setting the duration of said subsequent one of said first time intervals as a function of the time measured by said measuring means.

12. In a pacemaker of the type having:
(a) an atrial sense amplifier for producing atrial sense event signals in response to atrial depolarizations;
(b) a ventricular sense amplifier for producing ventricular sense event signals in response to ventricular depolarizations;
(c) a ventricular pulse generator for producing ventricular stimulating pulses in response to ventricular pace event signals;
(d) timing means for timing A-V escape intervals following the occurrences of said atrial sense event signals and for generating said ventricular pace event signals at the conclusion of each of said A-V escape intervals, said timing means further comprises means for generating a said ventricular pace event signal a predetermined time period following the generation of a previous said ventricular pace event signal, in the absence of said atrial sense event signals and said ventricular sense event signals, the improvement wherein;
(e) said timing means further comprises means for determining a first time interval following each said ventricular pace event signal and a second time interval following each said first time interval, said timing means initiating the timing of said A-V escape intervals in response to said atrial sense event signals occurring during said second time intervals, but not in response to said atrial sense event signals occurring during said first time intervals, said timing means further comprising means responsive to the occurrence of one of said atrial sense event signals within one of said second time intervals for decreasing the duration of the said first time interval following a subsequent one of said ventricular pace event signals.

13. A pacemaker according to claim 12 wherein said timing means further comprises means responsive to the lack of said atrial sense event signals during one of said time intervals for extending the duration of the same first time interval following a subsequent one of said ventricular pace event signals.

14. A pacemaker according to claim 12 or claim 13 wherein said timing means further comprises means responsive to the occurrence of one of said atrial sense event signals during one of said second time intervals for decreasing the duration of a subsequent one of said predetermined time periods and the said first time interval therein and means responsive to the lack of said atrial sense event signals during one of said second time intervals for increasing the duration of a subsequent one of said predetermined time periods and the duration of said first time interval therein.

15. A pacemaker according to claim 14 wherein said means responsive to the occurrence of one of said atrial sense event signals within one of said second time intervals for decreasing the duration of a subsequent one of said predetermined time periods comprises means for measuring the time between the occurrence of said one of said atrial sense event signals and the immediately preceding one of said ventricular pace event signals, said timing means further comprising means for setting the duration of said subsequent one of said predetermined time periods as a function of the measurement performed by said measuring means.

16. A pacemaker according to claim 12 wherein said means responsive to the occurrence of one of said atrial sense event signals within one of said second time intervals for decreasing the duration of the said first time intervals following a subsequent one of said ventricular pace event signals, further comprises means for measuring the time between the occurrence of said one of said atrial sense event signals and the immediately preceding one of said ventricular pace event signals, said timing means further comprising means for setting the duration of the said first time interval following said subsequent one of said ventricular pace signals as a function of the time measured by said measuring means.

17. In a pacemaker of the type having:
(a) an atrial sense amplifier for producing atrial sense event signals (AS) in response to atrial depolarizations;
(b) a ventricular sense amplifier for producing ventricular sense event signals (VS) in response to ventricular depolarizations;
(c) an atrial pulse generator for producing atrial stimulating pulses in response to atrial pace event signals (AP);
(d) a ventricular pulse generator for producing ventricular stimulating pulses in response to ventricular pace event signals (VP);
(e) timing means for timing V-A escape intervals and for generating said atrial pace event signals at the conclusion of said V-A escape intervals and for timing A-V escape intervals and for generating said ventricular pace event signals at the conclusion of said A-V escape intervals, said V-A escape intervals initiated by the occurrence of said ventricular pace event signals or said ventricular sense event signals, said A-V escape intervals initiated by the occurrence of said atrial sense event signals or said atrial pace event signals, the improvement wherein;
(f) said timing means includes means for dividing each said V-A escape interval into a first time interval and a second time interval, said timing means initiating timing of said A-V escape intervals in response to the occurrence of said atrial sense event signals during said second time intervals but not in response to the occurrence of said atrial sense event signals during said first time intervals, said timing means further comprising means for determining an inhibition interval K3 beginning a predetermined time prior to the expiration of each said V-A interval and means responsive to the occurrence of one of said atrial sense event signals which occurs in both the said first time interval and the said inhibition interval K3 during one of said V-A escape intervals for preventing the generation of an atrial stimulating pulse at the expiration of said one of said V-A time intervals and for initiating timing of said A-V escape interval at the expiration of said one of said V-A escape intervals.

18. A pacemaker according to claim 17 wherein said timing means further comprises means responsive to one of said atrial sense event signals occurring within one of said second time intervals to decrease the duration of a subsequent one of said V-A escape intervals.

19. A pacemaker according to claim 17 wherein said timing means comprises means responsive to one of said atrial sense event signals occurring within one of said second time intervals to decrease the duration of a subsequent one of said first time intervals.

20. A pacemaker according to claim 17 or claim 18 or claim 19 wherein said means responsive to the occurrence of one of said atrial sense event signals which occurs in both the said first time interval and the said inhibition interval K3 during one of said V-A escape intervals comprises means responsive to the occurrence of one of said atrial sense event signals during one of said time intervals for measuring an AS-AP interval which comprises the interval between the occurrence of said one of said atrial sense event signals and the expiration of said one of said V-A time intervals and for comparing said AS-AP interval to said inhibition interval K3 to determine whether said one of said atrial sense event signals also occurs within said inhibition interval K3.

21. A pacemaker according to claim 1 or claim 6 or claim 10 or claim 12 or claim 17 wherein said timing means further comprises means for determining an absolute refractory period following each said ventricular sense event signal and each said ventricular pace event signal during which said timing means is nonresponsive to said atrial event signals.

* * * * *